(12) United States Patent
Oshima

(10) Patent No.: US 12,196,824 B2
(45) Date of Patent: Jan. 14, 2025

(54) MEDICAL SYSTEM AND IMAGE-GENERATING METHOD

(71) Applicant: ASAHI INTECC CO., LTD., Seto (JP)

(72) Inventor: Fumiyoshi Oshima, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 130 days.

(21) Appl. No.: 18/078,757

(22) Filed: Dec. 9, 2022

(65) Prior Publication Data

US 2023/0103428 A1    Apr. 6, 2023

Related U.S. Application Data

(63) Continuation of application No. PCT/JP2021/017448, filed on May 7, 2021.

(30) Foreign Application Priority Data

Jun. 24, 2020    (JP) ................................. 2020-108725

(51) Int. Cl.
  *G01R 33/02*    (2006.01)
  *G01R 33/00*    (2006.01)

(52) U.S. Cl.
  CPC ......... *G01R 33/02* (2013.01); *G01R 33/0094* (2013.01)

(58) Field of Classification Search
  CPC .......................... G01R 33/02; G01R 33/0094
  See application file for complete search history.

(56) References Cited

U.S. PATENT DOCUMENTS

| | | | |
|---|---|---|---|
| 6,397,095 B1 * | 5/2002 | Eyuboglu | G01R 33/54 324/309 |
| 2017/0071499 A1 * | 3/2017 | Nebuya | A61B 5/0033 |
| 2019/0302195 A1 | 10/2019 | Honkura et al. | |

FOREIGN PATENT DOCUMENTS

| | | |
|---|---|---|
| EP | 3 111 837 A1 | 1/2017 |
| JP | 2009-538168 A | 11/2009 |
| JP | 2016-39914 A | 3/2016 |
| JP | 2017-217536 A | 12/2017 |
| JP | 2018-205102 A | 12/2018 |
| WO | 2007/138492 A2 | 12/2007 |
| WO | 2008/057573 A2 | 5/2008 |
| WO | 2012/045188 A1 | 4/2012 |

(Continued)

OTHER PUBLICATIONS

Jeong, W., et al., "Focused Current Density Imaging Using Internal Electrode in Magnetic Resonance Electrical Impedance Tomography (MREIT)," IEEE Transactions on Biomedical Engineering. vol. 61(7), 2014. p. 1938-1946 (Year: 2014).*

(Continued)

*Primary Examiner* — Sean A Frith
(74) *Attorney, Agent, or Firm* — Oliff PLC

(57) ABSTRACT

A medical system is provided with: a medical device that is inserted inside a living body; a distal end electrode that is disposed at a distal end of the medical device, and passes a high frequency to the living body from inside the living body; a magnetic sensor that is disposed outside the living body, and detects a magnetic field generated by the high frequency that has been passed from the distal end electrode to the living body; and an image generation portion that generates an internal image of the living body using magnetic field information output from the magnetic sensor.

9 Claims, 7 Drawing Sheets

(56) References Cited

FOREIGN PATENT DOCUMENTS

WO    2015/129756 A1    9/2015

OTHER PUBLICATIONS

Honkura, y., et al. "The Development of AASIC Type GSR Sensor Driven by GHz Pulse Current," MDPI Sensors. vol. 20(1023), 2020. p. 1-13 (Year: 2020).*

Woo Chul Jeong et al., "Focused Current Density Imaging Using Internal Electrode in Magnetic Resonance Electrical Impedance Tomography (MREIT)", IEEE Transactions on Biomedical Engineering, Feb. 21, 2004, Abstract, I. Introduction, II. Materials and Methods, pp. 1938-1946, vol. 61, No. 7, Jul. 2014.

Kim et al., "Magnetic flux density measurement in magnetic resonance electrical impedance tomography using a low-noise current source", Measurement Science and Technology, vol. 22, No. 10, Sep. 2, 2011, pp. 1-9.

* cited by examiner

MEDICAL SYSTEM AND IMAGE-GENERATING METHOD

CROSS REFERENCE TO RELATED APPLICATIONS

The present application is a Bypass Continuation of PCT/JP2021/017448, filed May 7, 2021, which is based upon and claims priority from Japanese Application No. 2020-108725 filed on Jun. 24, 2020, the entirety of the prior applications being hereby incorporated by reference into this application.

TECHNICAL FIELD

The disclosed embodiments relate to a medical system, and an image-generating method.

BACKGROUND ART

Conventionally, a technique is known that uses an electric current, a magnetic field, or ultrasound waves passing through a living body to generate an in-vivo image showing the internal structure of the living body, including the living tissues. For example, Patent Literature 1 discloses a technique that generates an in-vivo image by using an annular detection portion having electrodes and magnetic sensors alternately disposed side-by-side, passing an electric current between the electrodes disposed outside the measurement subject, and then detecting the magnetic field generated by the electric current at the magnetic sensors. Patent Literature 2 discloses a technique that generates an in-vivo image by wrapping a band having a plurality of electrodes arranged side-by-side around the chest of a test subject, injecting an electric current to a pair of electrodes among the plurality of electrodes, and measuring the electric current at each of the remaining electrodes. Patent Literature 3 discloses a technique that generates an in-vivo image by generating and detecting ultrasound waves from the distal end of a catheter.

CITATION LIST

Patent Literature

Patent Literature 1: WO2015/129756
Patent Literature 2: JP 2016-39914 A
Patent Literature 3: JP 2017-217536 A

SUMMARY

Technical Problems

However, even with the prior art described above, there is still room for further improvements to be made to the technique of generating an internal image of a living body. For example, in Patent Literature 1, the measurement subject is not positioned between the electrodes in locations where the pair of electrodes that exchange electric current are in close proximity to each other, and this sometimes causes the electric current to pass from one electrode to the other electrode without passing through the measurement subject. In this case, the generated magnetic field does not contain information relating to the internal structure of the living body (in-vivo information), which has the possibility of reducing the efficiency of the acquired in-vivo information. Furthermore, in Patent Literature 2, an in-vivo image is generated based on the electric current detected by the electrodes. An electric current is not as easily detected with high speed and high sensitivity compared to a magnetic field, which may cause a relative decrease in the resolution of the in-vivo image. In Patent Literature 3, an in-vivo image is generated by detecting reflected waves from each of the living tissues inside the living body. Inside a living body, ultrasound waves have a large difference in acoustic impedance with the neighboring tissue in the bones and calcified sites, and in the lungs and the like that contain air, which can cause the ultrasound waves to be in a state close to total reflection and prevent an image in the depth direction from being obtained.

The disclosed embodiments have been made to solve the above-described problems, and an object thereof is to provide a technique that improves the technique of generating an internal image of a living body.

Solutions to Problem

The disclosed embodiments have been made to solve at least some of the problems described above, and can be implemented as the following aspects.

(1) According to an aspect of the disclosed embodiments, a medical system is provided. This medical system is provided with: a medical device that is inserted inside a living body; a distal end electrode that is disposed at a distal end of the medical device, and passes a high frequency to the living body from inside the living body; a magnetic sensor that is disposed outside the living body, and detects a magnetic field generated by the high frequency that has been passed from the distal end electrode to the living body; and an image generation portion that generates an internal image of the living body using magnetic field information output from the magnetic sensor.

According to this configuration, the medical system detects the magnetic field generated by the high frequency that has been passed from the medical device inside the living body to the living body by using a magnetic sensor outside the living body, which enables the technique of generating an internal image of the living body to be improved.

(2) The medical system of the above aspect may further include a counter electrode plate that is disposed outside the living body, and is energized by the distal end electrode via the living body. According to this configuration, the magnetic field generated by the high frequency that has been passed from the medical device inside the living body toward the counter electrode plate outside the living body is detected by the magnetic sensor outside the living body, which enables in-vivo information to be more efficiently obtained from the detected magnetic field.

(3) In the medical system of the above aspect, a plurality of the magnetic sensors and the counter electrode plates may be alternately disposed side-by-side. According to this configuration, the magnetic field generated by the high frequency that has been passed from the medical device inside the living body toward the counter electrode plates outside the living body can be detected by the plurality of magnetic sensors in close proximity to the counter electrode plates. This enables in-vivo information to be more efficiently obtained from the detected magnetic field.

(4) In the medical system of the above aspect, the magnetic sensor may be a GSR sensor. According to this configuration, it is possible to improve the resolution of an in-vivo image by further increasing the detection accuracy of the magnetic field.

(5) In the medical system of the above aspect, a frequency of the high frequency that is passed by the distal end electrode may be 10 kHz to 10 MHz. According to this configuration, it is possible to generate an in-vivo image while suppressing the effects of the high frequency on the living body.

The disclosed embodiments may be realized in various modes, and may be realized in modes such as image generation devices, image-generating methods, examination devices, catheters, examination methods, production methods of medical systems, and computer programs.

DETAILED DESCRIPTION OF EMBODIMENTS

First Embodiment

<Overall Configuration of Medical System 1>

Figure 1:
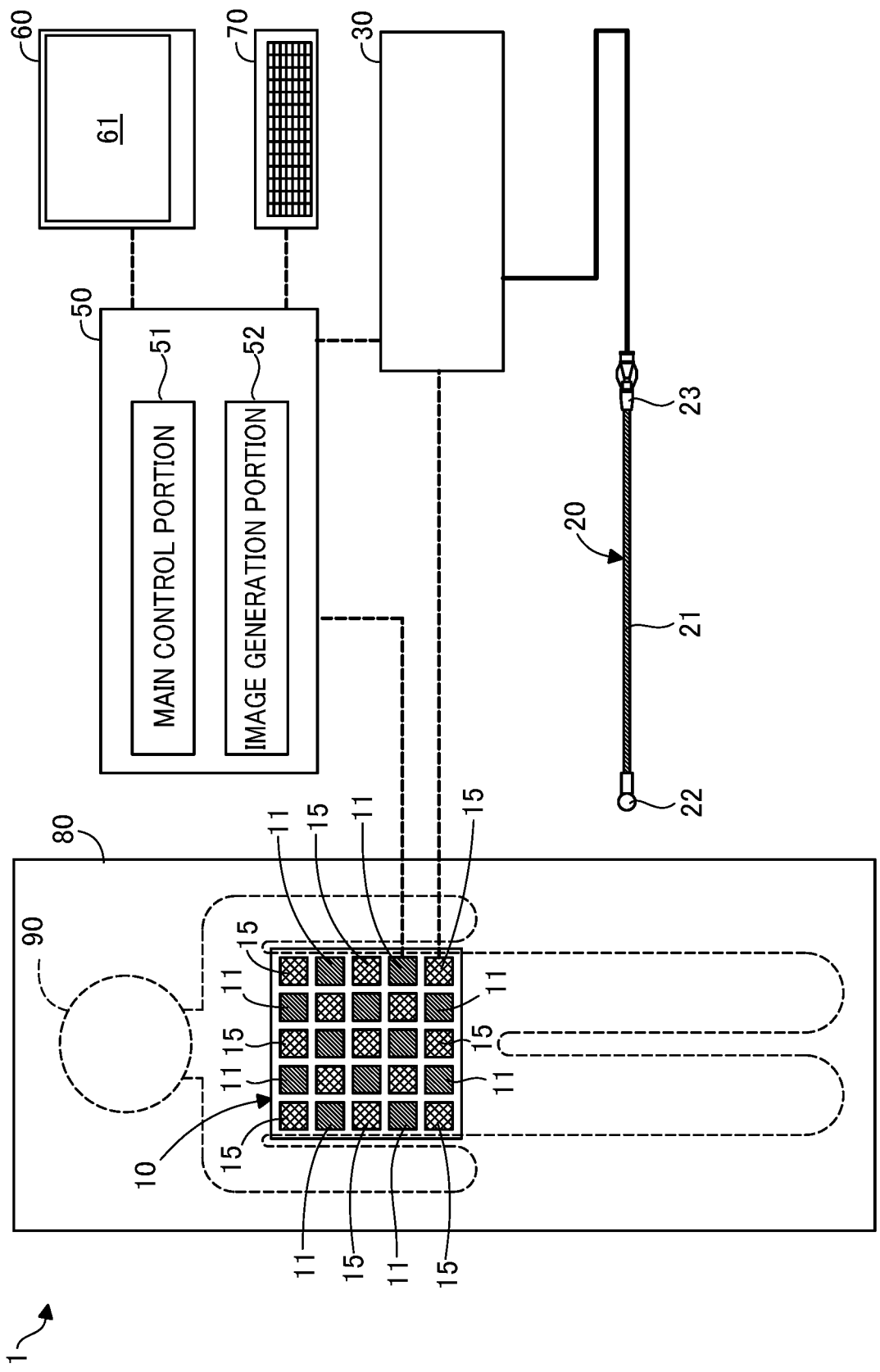
FIG. 1 is an explanatory diagram illustrating a schematic configuration of a medical system 1 according to a first embodiment.

FIG. 1 is an explanatory diagram illustrating a schematic configuration of a medical system 1 according to a first embodiment. A medical system 1 is a device that generates an in-vivo image (also referred to simply as an "internal image") showing the internal structure of a living body (in this case, a human body) 90 including the living tissue, and includes a sensor/electrode array 10, a catheter 20, a high-frequency generator 30, a computer 50, a monitor 60, and an operation portion 70.

The sensor/electrode array 10 is a device that detects the strength, the orientation, and the like of a magnetic field generated by a high frequency that is passed from the catheter 20 located inside the human body 90, and includes a plurality of magnetic sensors 11 and a plurality of counter electrode plates 15. The plurality of magnetic sensors 11 and the plurality of counter electrode plates 15 are alternately disposed side-by-side in both the vertical direction and the horizontal direction of the sensor/electrode array 10, and are disposed in a matrix form. The magnetic sensor 11 is a device that detects the strength and orientation of a magnetic field, and examples thereof may include a GSR (GHz-Spin-Rotation) sensor, a magnetoresistive effect device (MR), and a magnetic impedance device (MI). The counter electrode plate 15 is an energization electrode which is energized by the high frequency of the catheter 20 via the human body 90, and is electrically connected to the high-frequency generator 30.

Here, the sensor/electrode array 10 has a plurality of magnetic sensors 11 and counter electrode plates 15 attached to a flexible band member, and is secured to the human body 90 by being wrapped around the human body 90. The sensor/electrode array 10 is configured such that it can be maintained in a wrapped state around the human body 90. The sensor/electrode array 10 is configured such that it can be attached and detached at an arbitrary position of the human body 90. For example, it can be attached to the torso, arms, legs, neck, head, and the like of the human body 90. The sensor/electrode array 10 may be in direct contact with the body surface of the human body 90, or there may be a garment or a space between it and the body surface. The sensor/electrode array 10 may be configured in the form of a garment or a hat. In these cases, the magnetic sensors 11 and the counter electrode plates 15 may be provided along the shape of the human body 90. Furthermore, the sensor/electrode array 10 may be a plate-like panel that is disposed on one (one surface) or both (both surfaces) of the front and rear of the human body 90. Moreover, the sensor/electrode array 10 may be a plate-like panel that is disposed on one (one surface) or both (both surfaces) of the left and right sides of the human body 90. Also, the sensor/electrode array 10 may be embedded near the center of a table (bed) 80 on which the human body 90 lies.

The catheter 20 is inserted inside the human body 90 (in this case, inside a blood vessel), and generates a high frequency from the distal end inside the human body 90. The catheter 20 includes a main body portion 21, a distal end electrode 22, and a connector 23. The main body portion 21 has an elongated outer shape, and has a conductive core (not shown) provided inside an electrically insulating outer layer. The distal end electrode 22 is a tip provided on the distal end of the body portion 21 (distal tip), and is electrically connected to the distal end of the core wire. The connector 23 is provided on the proximal end of the body portion 21, and is connected to the high-frequency generator 30. The connection between the connector 23 and the high-frequency generator 30 results in the proximal end of the core wire being electrically connected to the high-frequency generator 30.

The high-frequency generator 30 is a device that supplies a high-frequency current to the catheter 20, and supplies a high-frequency current to the distal end electrode 22 via the core wire. The high-frequency generator 30 is also electrically connected to the counter electrode plates 15 of the sensor/electrode array 10, and causes energization between the distal end electrode 22 and the counter electrode plates 15 by supplying a high-frequency current to the distal end electrode 22. The high-frequency generator 30 is connected to the computer 50, and switches on and off the supply of the high-frequency current to the distal end electrode 22 according to instructions from the computer 50. The frequency of the high frequency supplied by the high-frequency generator 30 to the distal end electrode 22 of the catheter 20 is preferably 10 kHz to 10 MHz. This prevents the generation of heat when the high frequency is passed from the distal end electrode 22 to the human body 90.

The computer 50 is a device that controls the entire medical system 1, and is electrically connected to each of the sensor/electrode array 10, the high-frequency generator 30, the monitor 60, and the operation portion 70. The computer 50 includes a CPU, a ROM, and a RAM (not shown), and realizes the functions of a main control portion 51 and an image generation portion 52 when the CPU executes a program stored in the ROM.

The main control portion 51 exchanges information with the sensor/electrode array 10, the high-frequency generator 30, the monitor 60, and the operation portion 70, and controls the entire medical system 1. For example, when the main control portion 51 receives a predetermined operation via the operation portion 70, it controls the high-frequency generator 30 and supplies a high-frequency current to the distal end electrode 22. When the electric current is being supplied to the distal end electrode 22, the main control portion 51 acquires information relating to the strength and orientation of the magnetic field detected by the sensor/electrode array 10 (hereinafter also referred to as "magnetic field information").

The image generation portion 52 uses the magnetic field information output from the sensor/electrode array 10 to generate an internal image of the human body 90. The magnetic field information output from the sensor/electrode array 10 can sometimes contain a biomagnetic field. The image generation portion 52 can, for example, extract the magnetic field generated by the high frequency from the catheter 20 by using a high-pass filter to remove the biomagnetic field component from the magnetic field information. The image generation portion 52 generates an internal image of the human body 90 from the extracted magnetic field generated by the high frequency. An example of an internal image generated by the image generation portion 52 will be described later using FIG. 5.

The monitor 60 is a display portion that includes a display screen 61, and is configured by a liquid crystal display or the like. The medical system 1 may include a display portion other than the monitor 60. For example, the medical system 1 may include smart glasses including a display screen, or may include a projector that projects images. The operation portion 70 is configured by a keyboard or the like, and is operated, for example, when a technician of the catheter 20 switches the display content of the display screen 61. The operation portion 70 may be provided on a portion of the catheter 20.

Figure 2:
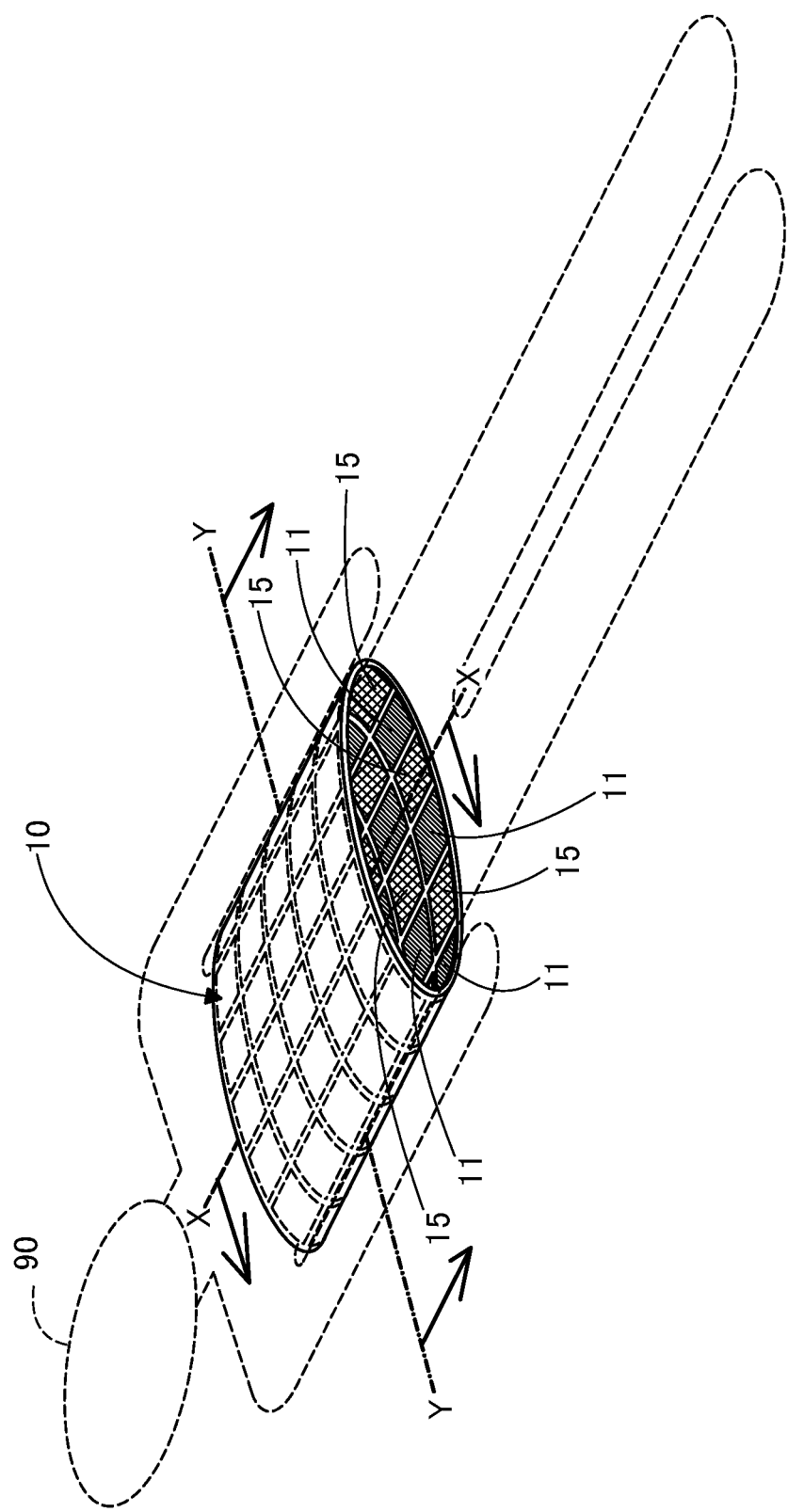
FIG. 2 is an explanatory diagram illustrating a configuration of a sensor/electrode array 10.

FIG. 2 is an explanatory diagram illustrating a configuration of the sensor/electrode array 10. The sensor/electrode array 10 has a rectangular band shape, and is configured so as to form a substantially annular shape by connecting one end portion in the longitudinal direction to the other end portion. The sensor/electrode array 10 has a plurality of magnetic sensors 11 and a plurality of counter electrode plates 15 attached to one surface that is wrapped around the human body 90 (the surface facing the human body 90). Hereinafter, the surface of the sensor/electrode array 10 that faces the human body 90 is also referred to as the inner surface, and the surface that does not face the human body 90 is also referred to as the outer surface. The magnetic sensors 11 and the counter electrode plates 15 may or may not be attached to the outer surface of the sensor/electrode array 10. The inner surface of the sensor/electrode array 10 has the magnetic sensors 11 and the counter electrode plates 15 alternately disposed in each of the vertical and horizontal directions.

Figure 3:
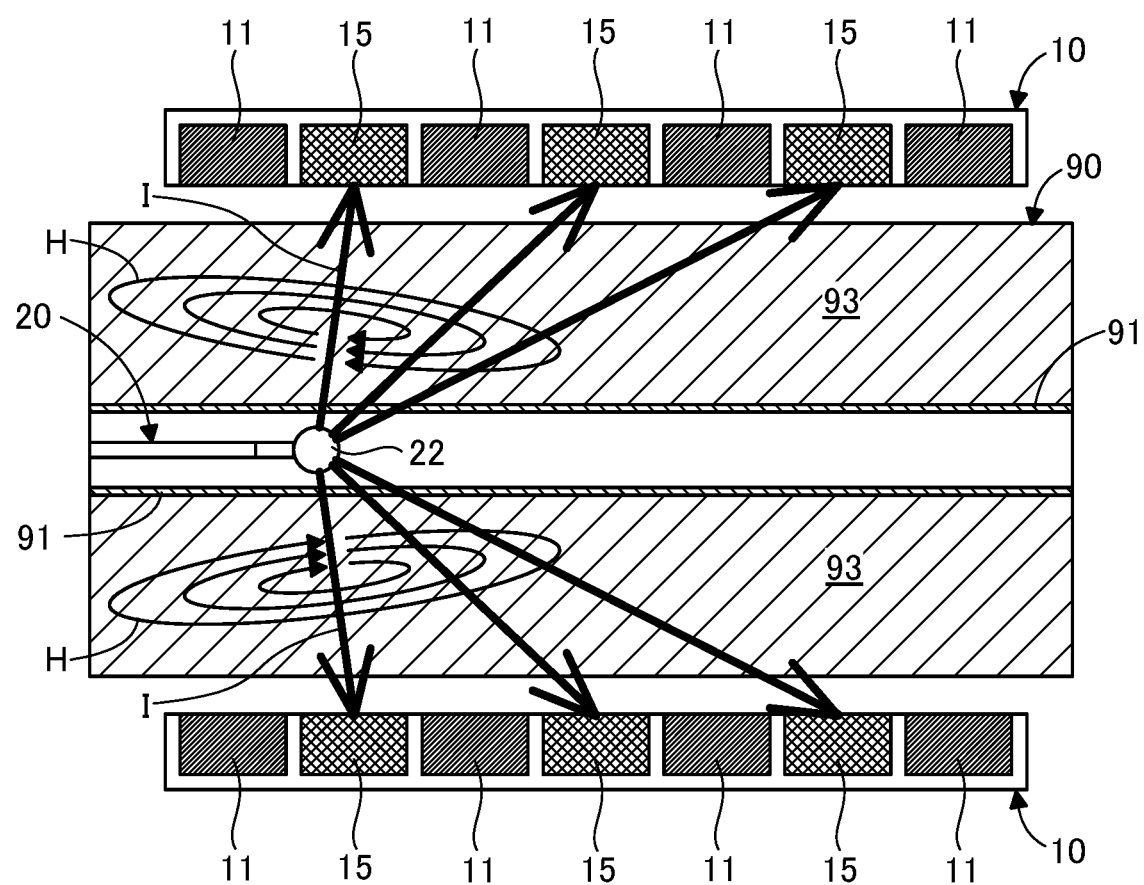
FIG. 3 is an explanatory diagram illustrating an X-X cross-section in FIG. 2.
Figure 4:
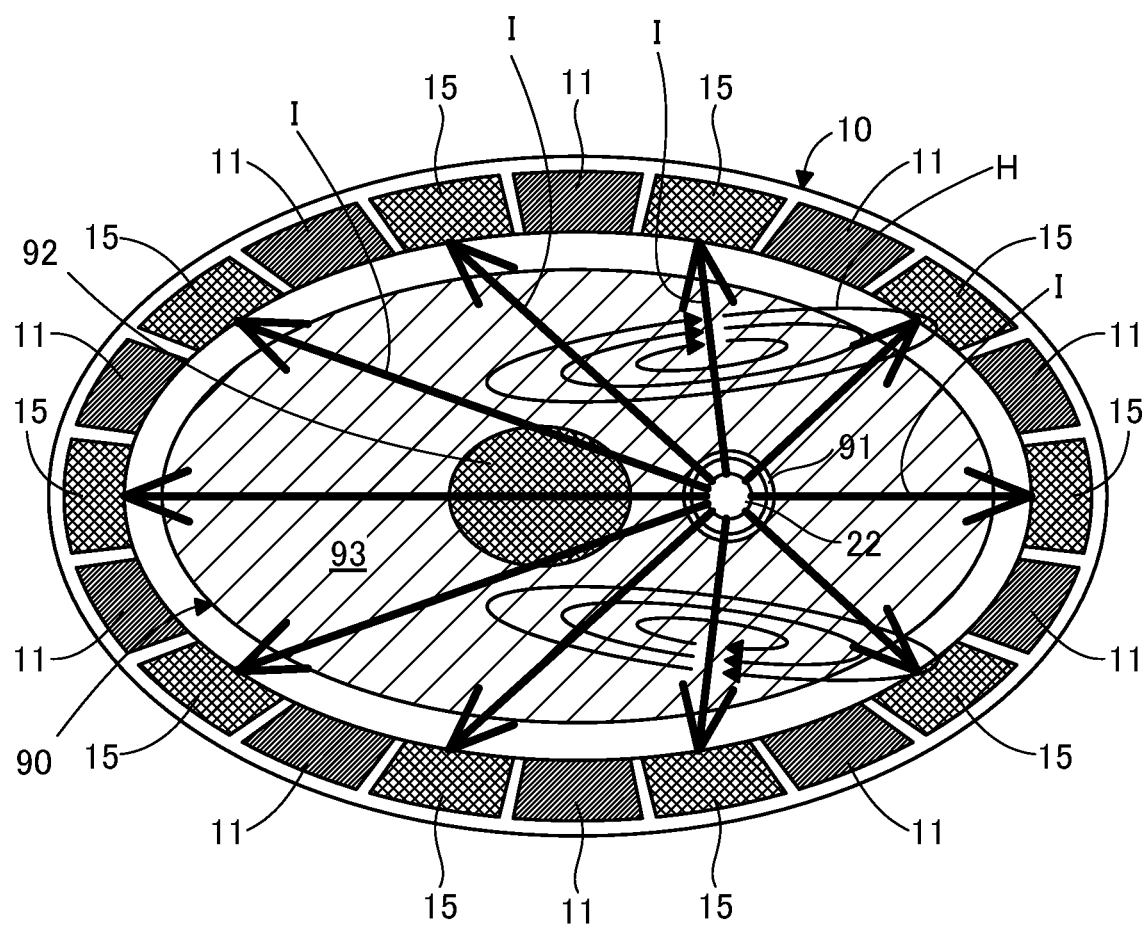
FIG. 4 is an explanatory diagram illustrating a Y-Y cross-section in FIG. 2.

FIG. 3 is an explanatory diagram illustrating an X-X cross-section in FIG. 2. FIG. 4 is an explanatory diagram illustrating a Y-Y cross-section in FIG. 2. FIG. 3 illustrates a longitudinal cross-section of the sensor/electrode array 10 and the human body 90, and FIG. 4 illustrates a transverse cross-section of the sensor/electrode array 10 and the human body 90. Here, the sensor/electrode array 10 is disposed outside the human body 90, and the catheter 20 is disposed inside the human body 90 (in this case, inside the blood vessel 91). When a high-frequency current I is passed from the distal end electrode 22 of the catheter 20 toward the counter electrode plates 15 outside the human body 90, a magnetic field H is generated around the current I. The generated magnetic field H is detected by the magnetic sensors 11, which enables magnetic field information that includes the in-vivo information of the human body 90 to be acquired. That is, the living tissues (such as the blood vessel 91, the bone 92, the muscle 93, and fat) inside the human body 90 have different electrical impedances to each other, which results in a change in the value of the high-frequency current I according to the path it takes inside the human body 90. Because the value of the magnetic field H also changes according to the value of the high-frequency current I, the magnitude and the orientation of the magnetic field H detected by each magnetic sensor 11 provided at each position of the sensor/electrode array 10, the relative timing in which each magnetic sensor 11 detects the magnetic field H, and the like, contains information such as the relative position, size, shape, and type of the living tissue (such as the blood vessel 91, the bone 92, the muscle 93, and fat) inside the human body 90 (in-vivo information). It is preferable to move the catheter 20 inside the blood vessel 91 in a state where it is generating a high frequency, because the magnetic field H can be detected at a wider variety of angles.

Figure 5:
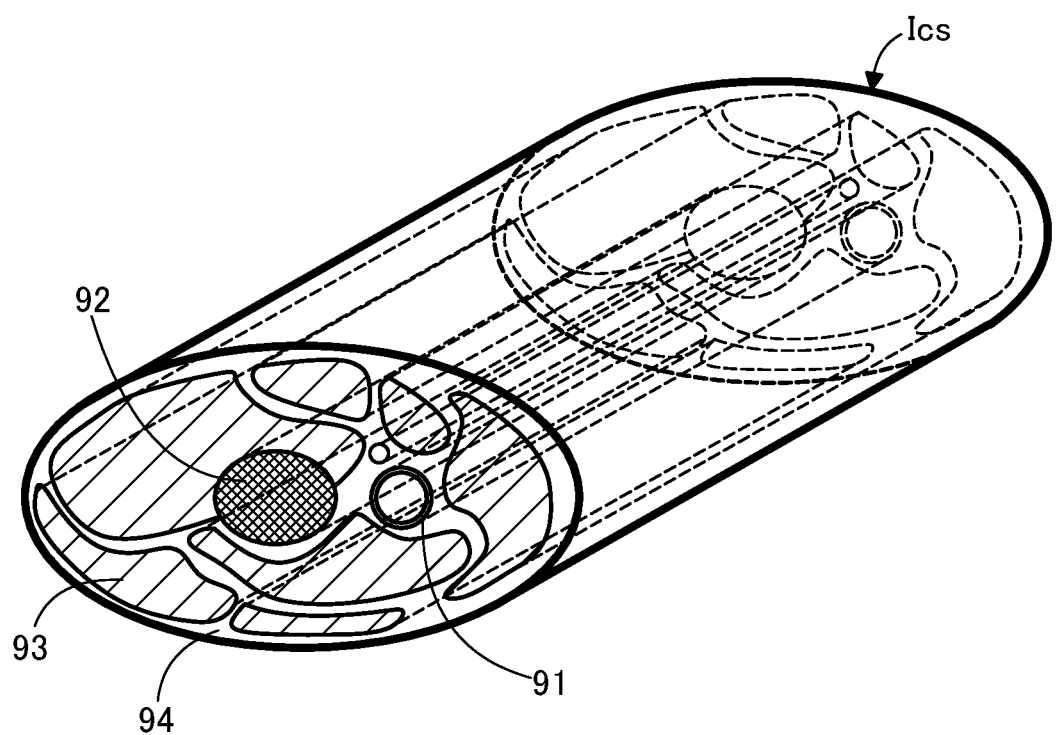
FIG. 5 is a diagram for describing a three-dimensional in-vivo image obtained from magnetic field information.

FIG. 5 is a diagram for describing a three-dimensional in-vivo image Ics of the human body 90 obtained from magnetic field information. The image generation portion 52 (FIG. 1) uses the magnetic field information output from the sensor/electrode array 10 to generate a three-dimensional in-vivo image Ics that three-dimensionally shows the internal structure of the human body 90, including the living tissues. The three-dimensional in-vivo image Ics shows the relative three-dimensional positions of each of the living tissues (such as the blood vessel 91, the bone 92, the muscle 93, and the fat 94) inside the human body 90. The image generation portion 52 is capable of generating an image (cross-sectional image) showing a cross-section of the three-dimensional in-vivo image Ics in an arbitrary plane that intersects the three-dimensional in-vivo image Ics. The cross-sectional image is an internal image showing the relative two-dimensional positions of each of the living tissues inside the human body 90. The main control portion 51 displays the generated cross-sectional images on the monitor 60.

Exemplary Effects of Present Embodiment

According to the medical system 1 of the present embodiment described above, because the magnetic field H generated by passing a high frequency from the catheter 20 inserted inside the human body 90 to the human body 90 is detected by magnetic sensors disposed outside the human body 90, the technique of generating an internal image of a living body can be improved. Conventionally, a technique is known in which an electric current is passed between electrodes disposed outside the measurement subject, and the magnetic field generated by the electric current is detected by magnetic sensors (for example, see WO2015/129756). In this case, the measurement subject is not positioned between the electrodes in locations where the pair of electrodes that exchange electric current are in close proximity to each other, and this causes the electric current to pass from one electrode to the other electrode without passing through the measurement subject. In this case, because the generated magnetic field does not contain information about the inside of the living body, the efficiency of acquiring the in-vivo information is reduced. On the other hand, according to the medical system 1 of the present embodiment, because a portion of the human body 90 is always located between the distal end electrode 22 inside the human body 90 and the counter electrode plates 15 outside the human body 90, the high frequency generated from the distal end electrode 22 always travels to the counter electrode plates 15 via the human body 90. This enables the in-vivo information to be efficiently obtained.

Furthermore, there is conventionally known a technique that generates an in-vivo image based on the electrical current detected by electrodes (for example, see JP 2016-39914 A). However, compared to a magnetic field, it is not easy to detect an electric current with high speed or high sensitivity, and this results in a problem with the resolution of the in-vivo image, and a resolution similar to that obtained with a CT, simple X-rays, or an MRI cannot be obtained. On the other hand, according to the medical system 1 of the present embodiment, because the magnetic field generated by the high-frequency current passed from the distal end electrode 22 inside the human body 90 toward the counter electrode plates 15 outside the human body 90 is detected, the detection can be performed faster and with greater sensitivity than a case where an electric current is detected. This enables the resolution of the in-vivo image to be further improved. Moreover, as shown in FIG. 3, it is possible to visualize an area further forward of the locations of the blood vessel 91 that the catheter 20 has passed through (all locations in which the counter electrode plates 15 and the magnetic sensors 11 are disposed on the body surface of the human body 90), which enables visualization of the front of an occluded part or the tip of a calcified section that could not be conventionally visualized. This enables the efficiency of the treatment to be improved. Further, according to the medical system 1 of the present embodiment, because a GSR sensor is used as the magnetic sensor 11, the magnetic field can be detected faster and with greater sensitivity.

Moreover, there is conventionally disclosed a technique that generates an in-vivo image by generating and detecting ultrasound waves from the distal end of a catheter (for example, see JP 2017-217536 A). However, due to the nature of ultrasound waves, when bones, calcified areas, or lungs that encapsulate air are present, it is not possible to visualize beyond these areas. Similarly, visualization is difficult with OCT catheters in the presence of blood due to the near-infrared wavelength, and visualization is not possible because light does not reach the depth direction of the tissue inside the living body. Furthermore, when visualization of the forward direction is attempted using a catheter or a guide wire, because the reception element is structurally small, there is a problem that only a small amount of information can be obtained. On the other hand, according to the medical system 1 of the present embodiment, as shown in FIG. 4, because the in-vivo image is generated using the magnetic field generated by the high-frequency current passed from the distal end electrode 22 inside the human body 90 toward the counter electrode plates 15 outside the human body 90, compared to a case where the in-vivo image is generated using ultrasound waves, even if bones, calcified areas, or lungs that encapsulate air are present, the entire area including these areas can be shown in the in-vivo image.

In addition, according to the medical system 1 of the present embodiment, because the magnetic sensors 11 and the counter electrode plates 15 are alternately disposed in each of the vertical and horizontal directions of the sensor/electrode array 10, it is possible to detect the magnetic field H generated by the high-frequency current I passed toward the counter electrode plates 15 at the plurality of magnetic sensors 11 adjacent to the counter electrode plates 15. As a result, the magnetic field H can be detected from a variety of angles from the outside of the human body 90, and the visible region inside the living body (region that can be displayed in the internal image) can be expanded. Furthermore, according to the medical system 1 of the present embodiment, because the frequency of the high frequency that is passed by the distal end electrode 22 is 10 kHz to 10 MHz, the in-vivo image can be generated while suppressing heating of the living body due to the high frequency.

Second Embodiment

Figure 6:
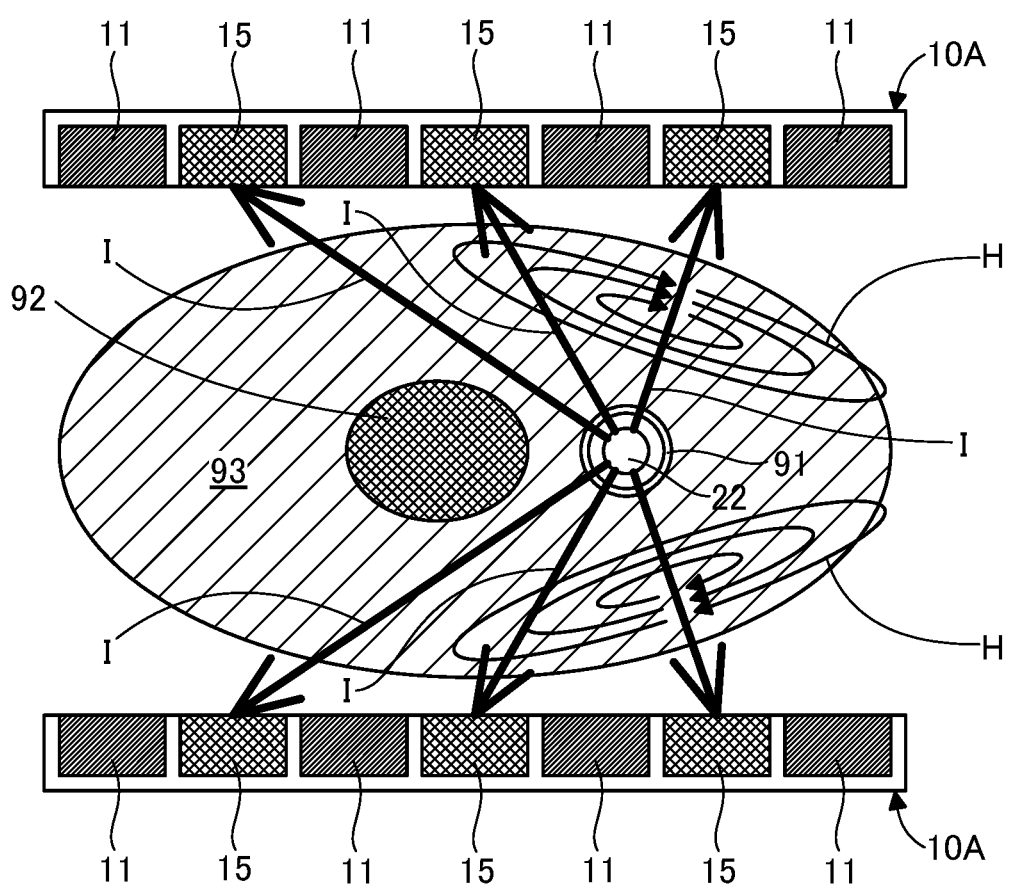
FIG. 6 is a diagram for describing a medical system 1A of a second embodiment.

FIG. 6 is a diagram for describing a medical system 1A of a second embodiment. FIG. 6 corresponds to FIG. 4 of the first embodiment. The medical system 1A of the second embodiment differs from the medical system 1 of the first embodiment in the configuration of the sensor/electrode array 10 (FIG. 4). The other aspects are the same as those of the medical system 1 of the first embodiment, and therefore the description is omitted. The medical system 1A of the second embodiment includes a sensor/electrode array 10A. FIG. 6 illustrates the sensor/electrode array 10A and a transverse cross-section of a human body 90. The sensor/electrode array 10A is disposed outside the human body 90, and the catheter 20 is disposed inside the human body 90 (inside the blood vessel 91).

The sensor/electrode array 10A is configured as a pair of plate-like panels, and the human body 90 is disposed between the pair of panels. Here, the panels are placed above and below the human body 90. A plurality of magnetic sensors 11 and a plurality of counter electrode plates 15 are disposed on each of the panels. The plurality of magnetic sensors 11 and the plurality of counter electrode plates 15 are alternately disposed side-by-side in both the vertical direction and the horizontal direction of the sensor/electrode array 10A, and on a single panel are disposed in a matrix form. When a high-frequency current I is passed from the distal end electrode 22 of the catheter 20 toward the counter electrode plates 15 of each panel, a magnetic field H is generated around the current I. The generated magnetic field H is detected by the magnetic sensors 11 adjacent to the counter electrode plates 15, which enables magnetic field information including in-vivo information of the human body 90 to be acquired.

According to the medical system 1A of the second embodiment described above, because the magnetic field H generated by passing a high frequency from the catheter 20 inserted inside the human body 90 to the human body 90 is detected by the magnetic sensors 11 disposed outside the human body 90, the technique of generating a cross-sectional image of a living body can be improved. As described in the second embodiment, the sensor/electrode array is not limited to being wrapped around the human body 90. As described in the present embodiment, the sensor/electrode array may be in the form of plate-like panels that are disposed on the front and rear of the human body 90. Furthermore, the sensor/electrode array may be in the form of plate-like panels disposed on both the left and right sides of the human body 90. Moreover, the sensor/electrode array may be a single panel disposed on the front, rear, or side of the human body 90.

Third Embodiment

Figure 7:
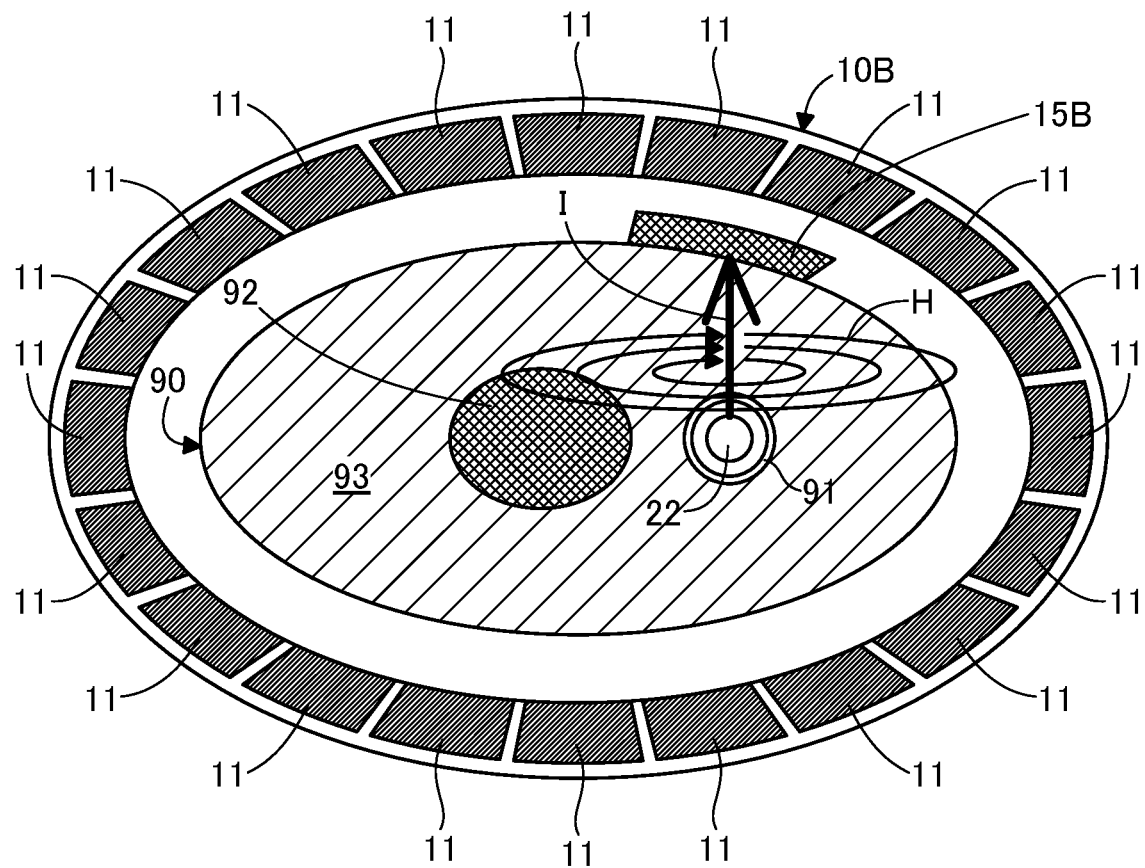
FIG. 7 is a diagram for describing a medical system 1B of a third embodiment.

FIG. 7 is a diagram for describing a medical system 1B of a third embodiment. FIG. 7 corresponds to FIG. 4 of the first embodiment. The medical system 1B of the third embodiment differs from the medical system 1 of the first embodiment in the configuration of the sensor/electrode array 10 (FIG. 4). The other aspects are the same as those of the medical system 1 of the first embodiment, and therefore the description is omitted. The medical system 1B of the third embodiment includes a sensor array 10B and a counter electrode plate 15B. FIG. 7 illustrates the sensor array 10B, the counter electrode plate 15B, and the transverse cross-section of a human body 90. The sensor array 10B and the counter electrode plate 15B are disposed outside the human body 90, and the catheter 20 is disposed inside the human body 90 (inside the blood vessel 91).

The sensor array 10B is provided with a plurality of magnetic sensors 11, but not counter electrode plates. The plurality of magnetic sensors 11 are arranged side-by-side in rows in both the vertical direction and the horizontal direction on one surface of the sensor array 10B, and are disposed in a matrix form. The sensor array 10B has a rectangular band shape, and is configured so as to form an annular shape by connecting one end portion in the longitudinal direction to the other end portion. The counter electrode plate 15B is configured as a separate member to the sensor array 10B, and is independently and directly attached to the human body 90. When a high-frequency current I is passed from the distal end electrode 22 of the catheter 20 toward the counter electrode plate 15B, a magnetic field H is generated around the current I. The generated magnetic field H is detected by the magnetic sensors 11 of the sensor array 10B, which enables magnetic field information including in-vivo information of the human body 90 to be acquired.

According to the medical system 1B of the third embodiment described above, because the magnetic field H generated by passing a high frequency from the catheter 20 inserted inside the human body 90 to the human body 90 is detected by the magnetic sensors 11 disposed outside the human body 90, the technique of generating a cross-sectional image of a living body can be improved. As described in the third embodiment, the sensor array 10B provided with the magnetic sensors 11 and the counter electrode plate 15B may be configured as separate members.

<Modifications>

The disclosed embodiments are not limited to the embodiments described above and may be carried out in various aspects without departing from the spirit thereof, and for example, the following modifications are possible.

[Modification 1]

The catheter 20 of the first to third embodiments may be configured as a so-called ablation catheter. Furthermore, in addition a high frequency, the catheter 20 may also generate plasma or irradiate laser light from the distal end. Moreover, the catheter 20 may be used for ablation, as well as for injecting drugs by puncture or for other purposes.

[Modification 2]

The medical systems 1, 1A and 1B of the first to third embodiments are provided with a distal end electrode 22 that generates a high frequency at the distal end of the catheter 20. However, the distal end electrode 22 may be provided in a location other than the distal end of the catheter 20. Furthermore, the medical system 1 of the present embodiment may be provided with a medical device other than the catheter 20 provided with the distal end electrode 22. For example, the medical system 1 may include, instead of the catheter 20, a guide wire or an endoscope provided with the distal end electrode 22.

[Modification 3]

The sensor/electrode arrays 10 and 10A of the first and second embodiments have the magnetic sensors 11 and the counter electrode plates 15 alternately disposed in the vertical direction and the horizontal direction. However, the magnetic sensors 11 and the counter electrode plates 15 may be alternately disposed in only one of the vertical direction and the horizontal direction. Furthermore, they do not have be alternately disposed in both directions. Even in this case, energization of the high frequency is possible due to the catheter 20 inside the human body 90 and the counter electrode plates 15 on the outside, and the magnetic field generated by the high frequency can be detected by the magnetic sensors outside the human body 90.

[Modification 4]

The medical systems 1, 1A and 1B of the first to third embodiments are provided with the counter electrode plates 15 and 15B. However, the medical system 1 does not have to include the counter electrode plates 15 and 15B. Even in this case, the magnetic field generated by the high frequency that has been passed from the catheter 20 inside the human body 90 to the human body 90 can be detected by the magnetic sensors 11 outside the human body 90.

[Modification 5]

In the first embodiment, the medical system 1 uses magnetic field information output from the sensor/electrode array 10 to generate the three-dimensional image Ics. However, the medical system 1 may be configured to generate only a cross-sectional image at a specific position of the human body 90, and not generate the three-dimensional in-vivo image Ics.

[Modification 6]

In the first embodiment, the medical system 1 may include a plurality of catheters 20 provided with the distal end electrode 22. Furthermore, the catheters 20 may be configured to be capable of passing an electric current from the distal end electrode 22 having a frequency outside the range of 10 kHz to 10 MHz.

[Modification 7]

The configuration of the present embodiment may also be applied to devices other than a medical system. For example, the configuration of the present embodiment may also be applied to examination systems, examination methods, image generation devices, image-generating methods, and the like.

The aspects have been above described above based on the embodiments and the modifications, but the embodiments of the aspects described above are provided to facilitate understanding the aspects and not to limit the aspects. The aspects may be modified and improved without departing from the spirit of the aspects and the scope of the claims, and equivalents thereof are included in the aspects. Further, unless the technical features are described as essential in the present specification, they may be omitted as appropriate.

DESCRIPTION OF REFERENCE NUMERALS 1, 1A, 1B Medical system
10, 10A Sensor/electrode array
10B Sensor array
11 Magnetic sensor
15, 15B Counter electrode plate
20 Catheter
21 Main body portion
22 Electrode
22 Distal end electrode
23 Connector
30 High-frequency generator
50 Computer
51 Main control portion
52 Image generation portion
60 Monitor
61 Display screen
70 Operation portion 90 Human body
91 Blood vessel

What is claimed is:

1. A medical system comprising:
a medical device configured to be inserted inside a living body;
a distal end electrode disposed at a distal end of the medical device, and configured to pass a high frequency to the living body from inside the living body;
a sensor/electrode array including
a plurality of magnetic sensors disposed outside the living body and configured to detect a magnetic field generated by the high frequency that is passed from the distal end electrode to the living body, and
a plurality of counter electrode plates disposed outside the living body and configured to be energized by the distal end electrode via the living body; and
a processor programmed to generate an internal image of the living body using magnetic field information output from the magnetic sensors, wherein
the plurality of magnetic sensors and the plurality of counter electrode plates are alternately disposed side-by-side in both a vertical column direction and a horizontal row direction of the sensor/electrode array.

2. The medical system according to claim 1, wherein each of the magnetic sensors is a GHz-Spin-Rotation (GSR) sensor.

3. The medical system according to claim 1, wherein a frequency of the high frequency that is passed by the distal end electrode is in a range from 10 kHz to 10 MHz.

4. The medical system according to claim 3, wherein each of the magnetic sensors is a GHz-Spin-Rotation (GSR) sensor.

5. The medical system according to claim 1, further comprising
a high-frequency generator configured to supply a high-frequency current to the distal end electrode to generate the high frequency.

6. A medical system comprising:
a medical device configured to be inserted inside a living body;
a distal end electrode disposed at a distal end of the medical device, and configured to pass a high frequency to the living body from inside the living body;
a sensor array including a plurality of magnetic sensors disposed outside the living body and configured to detect a magnetic field generated by the high frequency that is passed from the distal end electrode to the living body; and
a processor programmed to generate an internal image of the living body using magnetic field information output from the magnetic sensors, wherein
the plurality of magnetic sensors is disposed side-by-side directly adjacent to each other in both a vertical column direction and a horizontal row direction of the sensor array.

7. The medical system according to claim 6, wherein each of the magnetic sensors is a GHz-Spin-Rotation (GSR) sensor.

8. The medical system according to claim 6, wherein a frequency of the high frequency that is passed by the distal end electrode is in a range from 10 kHz to 10 MHz.

9. The medical system according to claim 6, further comprising
a high-frequency generator configured to supply a high-frequency current to the distal end electrode to generate the high frequency.

* * * * *